United States Patent [19]

Bittler et al.

[11] Patent Number: 4,859,659
[45] Date of Patent: Aug. 22, 1989

[54] DERMATICS UTILIZING 17β METHYL-18 NOR STEROIDS AND METHODS FOR THEIR USE

[75] Inventors: Dieter Bittler; Henry Laurent; Klaus Nickisch; Petra Rach, all of Berlin, Fed. Rep. of Germany

[73] Assignee: Schering Aktiengesellschaft, Berlin and Bergkamen, Fed. Rep. of Germany

[21] Appl. No.: 12,910
[22] PCT Filed: Apr. 10, 1986
[86] PCT No.: PCT/DE86/00156
 § 371 Date: Dec. 17, 1986
 § 102(e) Date: Dec. 17, 1986
[87] PCT Pub. No.: WO86/06078
 PCT Pub. Date: Oct. 23, 1986

[30] Foreign Application Priority Data

Apr. 17, 1985 [DE] Fed. Rep. of Germany ....... 3514272

[51] Int. Cl.$^4$ .......................... A61K 31/56; C07J 1/00
[52] U.S. Cl. .................... 514/177; 260/397.3
[58] Field of Search ...................... 260/397.3; 514/177

[56] References Cited
 FOREIGN PATENT DOCUMENTS
 1073309 6/1967 United Kingdom .

OTHER PUBLICATIONS

Pelc et al., Journal of the Chemical Society, Perkin Transactions, 1972, pp. 1219–1220.

Primary Examiner—Douglas W. Robinson
Assistant Examiner—Joseph A. Lipovsky
Attorney, Agent, or Firm—Millen, White & Zelano

[57] ABSTRACT

Dermatics are claimed which are characterized in that they contain as the active compound one or two 17β-methyl-18-nor steroids of general Formula I

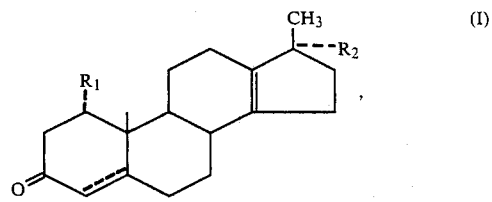

wherein
--- is a single bond or a double bond,
$R_1$ is a hydrogen atom or a methyl group, and
$R_2$ is an alkyl group of maximally 6 carbon atoms, optionally substituted by an alkanoyloxy group containing 2–6 carbon atoms.

25 Claims, No Drawings

DERMATICS UTILIZING 17βMETHYL-18 NOR STEROIDS AND METHODS FOR THEIR USE

The invention relates to the subject matter characterized by the claims.

Compounds of general Formula I according to claim 1 wherein $R_1$ means hydrogen and $R_2$ means a methyl group have been disclosed heretofore. Also, there are prior-art disclosures to the effect that 17,17-dimethyl-18-nor-4,13-androstadien-3-one and 17,17-dimethyl-18-nor-5α-androst-13-en-3-one exhibit a weak antiandrogenic activity upon systemic administration (Steroids 2: 185, 1963; and Steroids 4: 433, 1964). Furthermore, mention has been made in the literature of 17α-ethyl-17β-methyl-4,13-androstadien-3-one (Chem. Ber. 99: 3836, 1966; and Chem. Ber. 100: 1169, 1967) without any statements in regard to its pharmacological efficacy.

It has now been discovered that the aforementioned, previously known compounds and the remaining, previously unknown compounds of general Formula I as set out in claim 1 possess surprisingly a strong topical antiandrogenic activity upon epidermal application. In order to determine antiandrogenic efficacy, the influence on androgen-dependent lipogenesis by epidermal application of the compounds is analyzed as follows:

Male, fertile Syrian golden hamsters weighing about 80-100 g are castrated and substituted subcutaneously with 0.1 mg daily of testosterone propionate. The right ear of each test animal is treated twice daily with respectively 0.01 ml of a 1% strength solution of the test compound in acetone (or, in case of the control group, only with 0.01 ml of solvent) for three weeks. The animals are then sacrificed and in each case a defined tissue area of 8 mm diameter is punched out of the treated right ear as well as the untreated left ear.

The ventral and dorsal sides of the punched-out areas are separated along the auricular cartilage, transferred immediately into Dulbecco's modification of Eagle's medium to which has been added 4 millimoles of glutamine and 10% calf serum and which contains, to avoid microbial contamination, 100 IU/ml of penicillin, 100 μg/ml of streptomycin, 125 μg/ml of kanamycin, 25 IU/ml of nystatin, and 10 μg/ml gentamycin, and incubated for one hour at 37° C.

Thereafter, the punched-out tissues are introduced under sterile conditions into fresh culture medium containing 1 μCi/ml of $C^{14}$-tagged sodium acetate, and 4 hours at 37° C. Subsequently, the specimens are introduced into 2 ml of a proteolysis solution made up of 0.05 mole of tris buffer, pH 7.5, 0.01 mole of disodium edetate, 0.5% of sodium dodecyl sulfate, and 0.1% of proteinase K (company: E. Merck A.G., Darmstadt, Federal Republic of Germany), and incubated for 24 hours at 37° C.

The thus-obtained specimens are extracted once with 5 ml of chloroform and once more with 3 ml of chloroform, the combined chloroform extracts are concentrated under vacuum, and their content of radioactively labeled lipids is determined in a scintillation counter. The percentage inhibition of lipogenesis of the treated control group is calculated by comparison with the control group treated solely with solvent.

The table below shows the results obtained in these tests.

TABLE

| No. | Compound | Concentration % | Change of Lipogenesis % | |
|---|---|---|---|---|
| | | | Right Ear | Left Ear |
| 1 | 17,17-Dimethyl-18-nor-4,13-androstadien-3-one | 1.0 | −48 | −17 |
| | | 0.3 | −41 | −13 |
| | | 0.1 | −28 | −12 |
| 2 | 17α-Ethyl-17β-methyl-18-nor-4,13-androstadien-3-one | 1.0 | −31 | +9 |
| | | 0.3 | −27 | −14 |
| | | 0.1 | −20 | 0 |
| 3 | 1α,17,17-Trimethyl-18-nor-4,13-androstadien-3-one | 1.0 | −55 | −12 |
| | | 0.3 | −53 | −16 |
| | | 0.1 | −41 | −11 |
| 4 | 1α,17,17-Trimethyl-18-nor-5α-androst-13-en-3-one | 1.0 | −51 | −17 |
| | | 0.3 | −47 | −13 |
| | | 0.1 | −30 | −7 |
| 5 | 17α-Ethyl-1α,17β-dimethyl-18-nor-5α-androst-13-en-3-one | 1.0 | −48 | −20 |
| | | 0.3 | −40 | −9 |
| 6 | 1α,17β-Dimethyl-17α-propionyl-18-nor-5α-androst-13-en-3-one | 1.0 | −43 | +8 |
| 7 | 17α-(3-Acetoxypropyl)-17β-methyl-18-nor-4,13-androstadien-3-one | 1.0 | −40 | +13 |
| 8 | 1α,17β-Dimethyl-17α-(3-propionyloxypropyl)-18-nor-5α-androst-13-en-3-one | 1.0 | −40 | −17 |

When administered subcutaneously, the compounds of general Formula I according to claim 1 show an only low systemic antiandrogenic effectiveness, or none at all.

For the production of dermatics, the compounds of general Formula I according to claim 1 can be processed with the conventional excipients into solutions, gels, ointments, powders, or other preparations. Suitable excipients are, for example, water, ethanol, propanol, glycerol, methylcellulose, hydroxypropylcellulose, carboxypolymethylene, etc. The topically effective antiandrogen is present preferably in a concentration of 0.05-5.0% by weight, based on the total weight of preparation. The preparations can be utilized for the topical treatment of diseases such as acne, seborrhea, alopecia, and hirsutism.

The compounds of general Formula I according to claim 1 which can carry as the substituent $R_2$, for example, a methyl group, an ethyl group, a propyl group, a butyl group, a pentyl group, a hexyl group, an isopropyl group, a sec-butyl group, an isobutyl group, or a tert-butyl group—which groups can be substituted preferably by, for example, an acetoxy group, by a propionyloxy group, a butyryloxy group, a dimethylacetoxy group, a trimethylacetoxy group, a valeryloxy group, or a caproyloxy group—can be prepared in a conventional way. Suitable production methods are, for example, the processes characterized in claims 19 and 20 which can be performed under conditions well known to those skilled in the art (Steroids 4: 433 et seq., 1964; Chem. Ber. 99: 3836 et seq., 1966; and Chem. Ber. 100: 1169, 1967) and which will be described in greater detail in the examples below by means of typical representatives.

(A)

EXAMPLES RELATING TO THE PROCESS OF THIS INVENTION

EXAMPLE 1

A solution of 1.5 g of 17$\beta$-hydroxy-1$\alpha$-methyl-17$\alpha$-propyl-5$\alpha$-androstan-3-one in 45 ml of ethyl acetate and 6 ml of acetic anhydride is combined with 0.06 ml of 70% strength perchloric acid and stirred for 15 minutes at room temperature. The reaction solution is diluted with pyridine-containing ice water; the ethyl acetate phase is separated and washed with water. After drying and evaporation, 1.7 g of crude 3-acetoxy 1$\alpha$,17$\beta$-dimethyl-17$\alpha$-propyl-18-nor-5$\alpha$-androsta-2,13-diene is obtained.

A solution of 1.5 g of 3-acetoxy-1$\alpha$,17$\beta$-dimethyl-17$\alpha$-propyl-18-nor-5$\alpha$-androsta-2,13-diene in 30 ml of methanol and 15 ml tetrahydrofuran is stirred with 4.5 ml of concentrated hydrochloric acid for 17 minutes at room temperature. The reaction solution is diluted with diethyl ether, washed neutral with water, dried, and evaporared. The residue is chromatographed on silica gel. Yield: 1.04 g of 1$\alpha$17$\beta$-dimethyl-17$\alpha$-propyl-18-nor-5$\alpha$-androst-13-en-3-one, mp 88°–90° C.

EXAMPLE 2

A solution of 700 mg of 17$\beta$-hydroxy-1$\alpha$,17$\alpha$-dimethyl-5$\alpha$-androstan-3-one in 5 ml of 99% strength formic acid is stirred for 5 minutes at 100° C. The reaction solution is subsequently stirred into ice water; the thus-obtained precipitate is filtered off, washed with water, and taken up in dichloromethane. After drying and evaporation, the residue is recrystallized from methanol, yielding 350 mg of 1$\alpha$17,17-trimethyl-18-nor-5$\alpha$-androst-13-en-3-one, mp 135.7° C.

EXAMPLE 3

A solution of 6.5 g of 17$\alpha$-ethyl-3,3-ethylene-dioxy-1$\alpha$-methyl-5$\alpha$-androstan-17$\beta$-ol in 65 ml of 99% strength formic acid is stirred for 15 minutes at 100° C. and worked up as described in Example 2. Recrystallization from methanol yields 4.05 g of 17$\alpha$-ethyl-1$\alpha$,17$\beta$-dimethyl-18-nor-5$\alpha$-androst-13-en-3-one, mp 1226° C.

EXAMPLE 4

Under the conditions described in Example 2, 4.5 g of 17$\alpha$-butyl-17$\beta$-hydroxy-1$\alpha$-methyl-5$\alpha$-androstan-3-one is reacted and worked up. After chromatography on silica gel, 2.17 g of 17$\alpha$-butyl-1$\alpha$,17$\beta$-dimethyl-18-nor-5$\alpha$-androst-13-en-3-one is obtained as a viscous oil.

EXAMPLE 5

A solution of 1.0 g of 17$\beta$-hydroxy-17$\alpha$-(3-hydroxypropyl)-1$\alpha$-methyl-5$\alpha$-androstan-3-one in 10 ml of propionic acid is combined with 10 ml of concentrated hydrochloric acid and agitated at room temperature for 45 minutes. The reaction solution is diluted with diethyl ether, washed with water and sodium bicarbonate solution, dried, and evaporated. The residue is chromatographed on silica gel, thus producing 780 mg of 1$\alpha$,17$\beta$-dimethyl-17$\alpha$-(3-propionyloxypropyl)-18-nor-5$\alpha$-androst-13-en-3-one as a viscous oil.

EXAMPLE 6

Under the conditions set forth in Example 5, 1.0 g of 17$\beta$-hydroxy-17$\alpha$-(4-hydroxybutyl)-1$\alpha$-methyl-5$\alpha$-androstan-3-one is reacted and worked up. After chromatography on silica gel, 810 mg of 1$\alpha$,17$\beta$-dimethyl-17$\alpha$-(4-propionyloxybutyl)-18-nor-5$\alpha$-androst-13-en-3-one is obtained as a viscous oil.

EXAMPLE 7

A solution of 790 mg of 17$\beta$-hydroxy-1$\alpha$,17$\alpha$-dimethyl-4-androsten-3-one in 30 ml of concentrated formic acid is heated for 10 minutes to 100° C. The reaction mixture is diluted with water and extracted with diethyl ether. The extract is washed with water, dried, and concentrated under vacuum. The residue is chromatographed. The fractions eluted with 9–19% diethyl ether-pentane contain 500 mg which, recrystallized from pentane, yields 190 mg of 1$\alpha$,17,17-trimethyl-18-nor-4,13-androstadien-3-one, mp 69.5° C.

UV: $\epsilon_{241} = 12,800$.

EXAMPLE 8

Under the conditions described in Example 7, 1.0 g of 17$\beta$-hydroxy-1$\alpha$-methyl-17$\alpha$-pentyl-4-androsten-3-one is reacted. The crude product is chromatographed. The fractions eluted with 22–34% diethyl ether-pentane contain 1.08 g which, recrystallized from pentane, yields 460 mg of 1$\alpha$,17$\beta$-dimethyl-17$\alpha$-pentyl-18-nor-4,13-androstadien-3-one, mp 59.1° C.

UV: $\epsilon_{240} = 13,500$.

EXAMPLE 9

Under the conditions described in Example 7, 1.0 g of 17$\alpha$-(4-acetoxybutyl)-17$\beta$-hydroxy-1$\alpha$-methyl-4-androsten-3-one is reacted. The crude product is chromatographed. With 38–44% diethyl ether-pentane, 356 mg of 17$\alpha$-(4-acetoxybutyl)-1$\alpha$,17$\beta$-dimethyl-18-nor-4,13-androstadien-3-one is eluted in the form of a viscous oil.

UV: $\epsilon_{241} = 12,600$.

EXAMPLE 10

A solution of 20.0 g of 17$\beta$-hydroxy-17$\alpha$-methyl-4-androsten-3-one in 76 ml of concentrated formic acid is heated for 10 minutes to 100° C. The reaction solution is diluted with water and extracted with diethyl ether. The extract is washed with water, dried, and concentrated under vacuum. The residue is chromatographed, thus obtaining 15.80 g of 17,17-dimethyl-18-nor-4,13-androstadien-3-one in the shape of an oil which solidifies in crystalline form after some time. Melting point 68° C.

UV: $\epsilon_{238} = 16,200$.

EXAMPLE 11

Under the conditions set forth in Example 10, 2.0 g of 17$\beta$-hydroxy-17$\alpha$-methyl-5$\alpha$-androstan-3-one is converted into 17,17-dimethyl-18-nor-5$\alpha$-androst-13-en-3-one. Yield: 1.68 g, mp 139.0° C.

EXAMPLE 12

3.0 g of 17α-ethyl-17β-hydroxy-4-androsten-3-one is reacted under the conditions disclosed in Example 10. The crude product is chromatographed. The fractions eluted with 39-44% diethyl ether-pentane contain 2.45 g of oily 17α-ethyl-17β-methyl-18-nor-4,13-androstadien-3-one which, after having been allowed to stand, solidifies in crystalline form. Melting point 56.2° C.

UV: $\varepsilon_{238}=16,100$.

EXAMPLE 13

A solution of 1.0 g of 17β-hydroxy-17α-propyl-4-androsten-3-one in 2 ml of acetic acid and 2 ml of concentrated hydrochloric acid is stirred for 40 minutes at room temperature. The reaction mixture is diluted with water and extracted with dichloromethane. The organic phase is washed neutral with water, dried, and evaporated under vacuum. The crude product is purified by chromatography, thus obtaining 666 mg of 17β-methyl-17α-propyl-18-nor-4,13-androstadien-3-one as a viscous oil which, after some time, solidifies in crystalline form. Melting point 80.3° C.

UV: $\varepsilon_{240}=16,300$.

EXAMPLE 14

Under the conditions set forth in Example 13, 1.0 g of 17α-(3-acetoxypropyl)-17β-hydroxy-4-androsten-3-one is converted into 17α-(3-acetoxypropyl)-17β-methyl-18-nor-4,13-androstadien-3-one. Yield: 670 mg (oily).

UV: $\varepsilon_{240}=16,300$.

EXAMPLE 15

Under the conditions of Example 13, but using propionic acid in place of acetic acid, 1.0 g of 17β-hydroxy-17α-(4-propionyloxybutyl)-4-androsten-3-one is converted into 17β-methyl-17α-(4-propionyloxybutyl)-18-nor-4,13-androstadien-3-one. Yield: 667 mg (oily).

UV: $\varepsilon_{241}=16,100$.

(B) EXAMPLES RELATING TO PHARMACEUTICAL PREPARATIONS

EXAMPLE 1

(a) Preparation of the Oil/Water Emulsion 10.00 g of disodium edetate and 10.00 g of chlorquinaldol are dissolved in 300.00 g of purified, demineralized water and combined with 10.00 g of "Carbopol".

This mixture is introduced under vigorous agitation into a melt of 80.00 g of "Vaseline" (DAB 8)—DAB being the abbreviation for "Deutsches Arzneibuch" [German Pharmacopoeia], official issue, 8th edition, 1978—40.00 g of stearyl alcohol, 30.00 g of "MYRJ", and 50.00 g of jojoba oil. The mixture is stirred until an emulsion is produced having a particle size of 20-70 μm.

(b) Preparation of the Water/Oil Emulsion 230.00 g of purified, demineralized water is introduced under vigorous agitation into a melt of 220.00 g of "Vaseline" (DAB 8), 10.00 g of "Dehymuls" and 10.00 g of cera alba. The mixture is stirred until an emulsion is produced having a particle size of 20-70 μm.

(c) Production of a Cream

The water/oil emulsion is introduced under vigorous agitation under a vacuum of 10 torr into the oil/water emulsion. Stirring is continued until a dispersion is formed having a particle size of 10-50 μm, and the vacuum is lifted.

Under agitation, 5.000 g of 17α,17β-dimethyl-18-nor-4,13-androstadien-3-one—micronized; particle size predominantly 1-20 μm—is added into 95.000 g of this ointment base, and the agitation is continued until the active agent has been uniformly distributed in the ointment base.

EXAMPLE 2

97.000 g of the ointment base produced accordi to Example 1(c) is combined with 8.000 g of 1α,17,17-trimethyl-18-nor-5α-androst-13-en-3-one—micronized; particle size predominantly 1-20 μm—and the mixture is stirred until the active agent has been uniformly distributed in the ointment base.

EXAMPLE 3

95.000 g of the ointment base prepared according to Example 1(c) is combined with 5.000 g of 17α-ethyl-1α,17β-dimethyl-18-nor-5α-androst-13-en-3-one—micronized; particle size predominantly 1-20 μm—and the mixture is stirred until the active ingredient has been uniformly distributed in the ointment base.

EXAMPLE 4

95.000 g of the ointment base produced as described in Example 1(c) is combined with 5.000 g of 17α-(3-acetoxypropyl)-17β-methyl-18-nor-4,13-androstadien-3-one and the mixture is stirred until the active compound has been uniformly distributed in the ointment base.

EXAMPLE 5

45.000 g of "Vaseline" (DAB 8), 19.600 g of paraffin oil, 5.000 g of cetyl alcohol, 5.000 g of beeswax, and 5.000 g of sorbitan sesquinolate are melted together, combined with a solution of 0.2000 g of p-hydroxybenzoic acid ester in 15.2 g of demineralized water and emulsified at 50° C. The emulsion is then allowed to cool down, combined with 5.000 g of 1α,17,17-trimethyl-18-nor-4,13-androstadien-3-one—micronized; particle size predominantly 1-20 μm—and stirred until the active agent has been uniformly distributed in the ointment base.

We claim:

1. Dermatics, in the form of a solution, ointment, cream, or lotion for topical, substantially nonsystemic administration, characterized by containing as the active compound an antiandrogenically effective concentration of a 17β-methyl-18-nor steroid of general Formula I

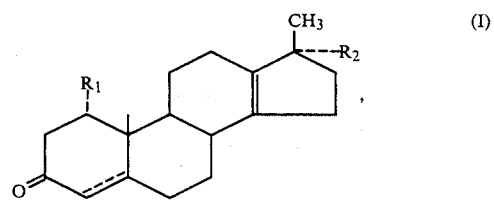

wherein is a single bond or a double bond, $R_1$ is a hydrogen atom or a methyl group, and $R_2$ is an alkyl group of maximally 6 carbon atoms, optionally substituted by an alkanoyloxy group containing 2-6 carbon atoms, and further comprising a dermatically acceptable excipient.

2. Dermatics according to claim 1 in the form of an ointment.

3. Dermatics according to claim 2, wherein the ointment is prepared by the steps of:
  (a) preparing an oil/water emulsion, by dissolving disodiuim edatate and chloroquinol in purified, demineralized water and combining with "Carbopol", introducing the mixture under vigorous agitation into a melt of "Vaseline", steryl alcohol, "MYRJ", and jojoba oil; and stirring the resulting mixture until an emulsion having a particle size of 20–70 μm is produced;
  (b) preparing a water/oil emulsion, by introducing purified, demineralized water under vigorous agitation into a melt of "Vaseline", "Dehymuls" and cera alba, and stirring until an emulsion having a particle size of 20–70 μm is produced;
  (c) preparing an ointment base, by introducing the water/oil emulsion of step (b) under vigorous agitation under a vacuum into the oil/water emulsion of step (a), stirring until a dispersion having a particle size of 10–50 μm is formed, and then lifting the vacuum; and
  (d) preparing the ointment by adding the active compound, in micronized form, having a particle size predominantly 1–20 μm, under agitation into the ointment base of step (c), and agitating this mixture until the active compound is uniformly distributed.

4. Dermatics according to claim 1, wherein $R_2$ is an alkyl group of 1–6 carbon atoms, substituted by an alkanoyloxy group containing 2–6 carbon atoms.

5. A dermatic according to claim 1, wherein the active compound is 17α,17β-dimethyl-18-nor-4,13-androstadien-3-one.

6. A dermatic according to claim 1, wherein the active compound is 1α,17,17-trimethyl-18-nor-5α-androst-13-en-3-one.

7. A dermatic according to claim 1, wherein the active compound is 17α-ethyl-1α,17β-dimethyl-18-nor-5α-androst-13-en-3-one.

8. A dermatic according to claim 1, wherein the active compound is 17α-(3-acetoxypropyl)-17β-methyl-18-nor-4,13-androstadien-3-one.

9. A dermatic according to claim 1, wherein the active compound is 1α,17β-dimethyl-17α-(3-propionyloxypropyl)-18-nor-5α-androst-13-en-3-one.

10. A dermatic according to claim 1, wherein the active compound is 1α,17β-dimethyl-17α-(4-propionyloxybutyl)-18-nor-5α-androst-13-en-3-one.

11. A dermatic according to claim 1, wherein the active compound is 17α-(4-acetoxybutyl)-1α,17β-dimethyl-18-nor-4,13-androstadien-3-one.

12. A dermatic according to claim 1, wherein the active compound is 17β-methyl-17α-(4-propionyloxybutyl)-18-nor-4,13-androstadien-3-one.

13. Dermatics according to claim 1 in the form of a solution.

14. Dermatics according to claim 1 in the form of a cream.

15. Dermatics according to claim 1 in the form of a lotion.

16. 17β-Methyl-18-nor steroids of general Formula Ia

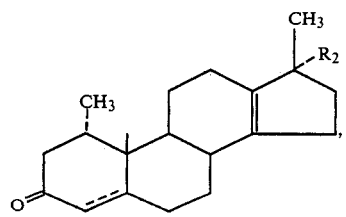

wherein
 represents a single bond or a double bond and
 $R_2$ is an alkyl group of maximally 6 carbon atoms, substituted by an alkanoyloxy group containing 2–6 carbon atoms.

17. 1α,17β-Dimethyl-17α-(3-propionyloxypropyl)-18-nor-5α-androst-13-en-3-one a compound of claim 16.

18. 1α,17β-Dimethyl-17α-(4-propionyloxybutyl)-18-nor-5α-androst-13-en-3-one a compound of claim 16.

19. 17α-(4-Acetoxybutyl)-1α,17β-dimethyl-18-nor-4,13-androstadien-3-one a compound of claim 16.

20. 17β-Methyl-18-nor steroids of general Formula Ib

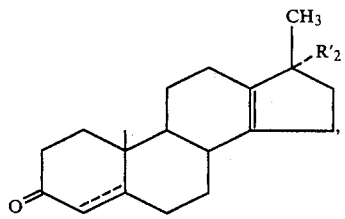

wherein
 represents a single bond or a double bond and
 $R'_2$ is an alkyl group of 3–6 carbon atoms, substituted by an alkanoyloxy group containing 2–6 carbon atoms.

21. 17α-(3-Acetoxypropyl)-17β-methyl-18-nor-4,13-androstadien-3-one a compound of claim 20.

22. 17β-Methyl-17α-(4-propionyloxybutyl)-18-nor-4,13-androstadien-3-one a compound of claim 20.

23. A method for treatment of an epidermal condition caused at least in part by excess androgen comprising administering topically an antiandrogenically-effective amount of a compound to the epidermis of an animal, wherein the compound is one or two 17β-methyl-18-nor steroids of the general Formula I

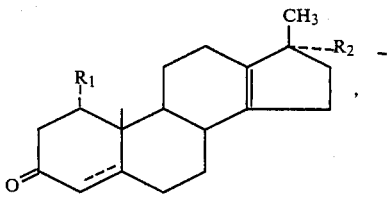

wherein
 is a single bond or a double bond,
 $R_1$ is a hydrogen atom ora methyl group, and
 $R_2$ is an alkyl group of 1–6 carbon atoms, optionally substituted by an alkanoyloxy group containing 2–6 carbon atoms.

24. A method of claim 23, wherein the disease is acne, seborrhea, alopecia, or hirsutism.

25. A method of claim 23, wherein $R_2$ is an alkyl group of 1–6 carbon atoms, substituted by an alkanoyloxy group containing 2–6 carbon atoms.

* * * * *

UNITED STATES PATENT AND TRADEMARK OFFICE
CERTIFICATE OF CORRECTION

PATENT NO. : 4,859,659

DATED : August 22, 1989

INVENTOR(S) : BITTLER ET AL

It is certified that error appears in the above-identified patent and that said Letters Patent is hereby corrected as shown below:

Column 6, claim 1, line 64:

reads "is a single or a double bond,"

should read -- ---- is a single bond or a double bond, --

Column 8, claim 16, line 11:

reads "wherein"

should read -- wherein --

Column 8, claim 16, line 12:

reads "represents a single bond or a double bond and"

should read -- ---- represents a single bond or a double bond and --

Column 8, claim 20, line 34:

reads "wherein"

should read -- wherein --

UNITED STATES PATENT AND TRADEMARK OFFICE
CERTIFICATE OF CORRECTION

PATENT NO. : 4,859,659
DATED : August 22, 1989
INVENTOR(S) : BITTLER ET AL

It is certified that error appears in the above-identified patent and that said Letters Patent is hereby corrected as shown below:

Column 8, claim 20, line 35:

reads "represents a single bond or a double bond and"

should read -- ---- represents a single bond or a double bond and --

Column 8, claim 23, line 57:

reads "wherein"

should read -- wherein --

Column 8, claim 23, line 58:

reads "is a single bond or a double bond,"

should read -- ---- is a single bond or a double bond, --

Signed and Sealed this

Seventh Day of August, 1990

*Attest:*

*Attesting Officer*

HARRY F. MANBECK, JR.

*Commissioner of Patents and Trademarks*